US011707269B2

United States Patent
O'Connell et al.

(10) Patent No.: US 11,707,269 B2
(45) Date of Patent: *Jul. 25, 2023

(54) SURGICAL RETRACTOR

(71) Applicant: NuVasive, Inc., San Diego, CA (US)

(72) Inventors: Casey O'Connell, San Diego, CA (US); James Coleman Lee, San Diego, CA (US); Joel Kohn, San Diego, CA (US); David Banks, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 395 days.

This patent is subject to a terminal disclaimer.

(21) Appl. No.: 16/849,787

(22) Filed: Apr. 15, 2020

(65) Prior Publication Data

US 2020/0237359 A1 Jul. 30, 2020

Related U.S. Application Data

(63) Continuation of application No. 15/386,999, filed on Dec. 21, 2016, now Pat. No. 10,653,407.

(51) Int. Cl.
*A61B 17/02* (2006.01)
*A61B 90/57* (2016.01)

(52) U.S. Cl.
CPC ........ *A61B 17/025* (2013.01); *A61B 17/0206* (2013.01); *A61B 17/0218* (2013.01); *A61B 17/0293* (2013.01); *A61B 90/57* (2016.02); *A61B 2017/0262* (2013.01)

(58) Field of Classification Search
CPC .............. A61B 17/025; A61B 17/0206; A61B 17/0218; A61B 17/0293; A61B 90/57; A61B 2017/0262

USPC ............................... 600/201–245; 606/53–59
See application file for complete search history.

(56) References Cited

U.S. PATENT DOCUMENTS

| 2,053,868 A | 9/1936 | Grosso |
| 2,623,517 A | 12/1952 | Barlow et al. |
| 3,168,093 A | 2/1965 | Gauthier |
| 3,221,743 A | 12/1965 | Thompson et al. |

(Continued)

FOREIGN PATENT DOCUMENTS

WO 2015054070 A1 4/2015

OTHER PUBLICATIONS

International Search Report for PCT/US17/17700, ISA, dated May 19, 2017, pp. 5.

(Continued)

*Primary Examiner* — Eduardo C Robert
*Assistant Examiner* — Tara Rose E Carter
(74) *Attorney, Agent, or Firm* — Seager, Tufte & Wickhem, LLP

(57) ABSTRACT

A surgical retractor assembly is provided that can assume both open and closed positions, and is easily convertible from one position to the other. The retractor assembly involves an arcuate frame member that can be engaged to an arcuate connector, which together form a generally circular or elliptical retractor frame assembly. The frame member has a groove for the insertion of one or more mobile carriages that hold retractor blade posts and allow the posts to move in multiple directions. The carriages may be locked to prevent movement in one or more directions, as well.

20 Claims, 12 Drawing Sheets

(56) References Cited

U.S. PATENT DOCUMENTS

| | | | |
|---|---|---|---|
| 3,522,799 A * | 8/1970 | Gauthier | A61B 17/0293 |
| | | | 600/233 |
| 3,724,449 A | 4/1973 | Gauthier | |
| 3,749,088 A | 7/1973 | Kohlmann | |
| 3,965,890 A | 6/1976 | Gauthier | |
| 4,010,741 A | 3/1977 | Gauthier | |
| 4,099,521 A | 7/1978 | Nestor et al. | |
| 4,254,763 A | 3/1981 | McCready et al. | |
| 4,434,791 A * | 3/1984 | Darnell | A61B 17/0293 |
| | | | 600/233 |
| 4,457,300 A | 7/1984 | Budde | |
| 4,510,926 A | 4/1985 | Inaba | |
| 4,617,916 A | 10/1986 | LeVahn et al. | |
| 4,971,038 A | 11/1990 | Farley | |
| 5,025,780 A | 6/1991 | Farley | |
| 5,242,240 A | 9/1993 | Gorham | |
| 5,400,772 A | 3/1995 | LeVahn et al. | |
| 5,529,358 A | 6/1996 | Dinkler et al. | |
| 5,616,117 A | 4/1997 | Dinkler et al. | |
| 5,792,046 A | 8/1998 | Dobrovolny | |
| 5,897,087 A | 4/1999 | Farley | |
| 5,899,627 A | 5/1999 | Dobrovolny | |
| 5,902,233 A | 5/1999 | Farley et al. | |
| 5,951,467 A | 9/1999 | Picha et al. | |
| 5,967,973 A | 10/1999 | Sherts et al. | |
| 5,984,865 A | 11/1999 | Farley et al. | |
| 6,017,008 A | 1/2000 | Farley | |
| 6,033,363 A | 3/2000 | Farley et al. | |
| 6,083,154 A | 7/2000 | Liu et al. | |
| 6,102,854 A | 8/2000 | Cartier et al. | |
| 6,190,312 B1 | 2/2001 | Fowler, Jr. | |
| 6,213,940 B1 | 4/2001 | Sherts et al. | |
| 6,231,506 B1 | 5/2001 | Hu et al. | |
| 6,254,532 B1 * | 7/2001 | Paolitto | A61B 17/0206 |
| | | | 600/235 |
| 6,264,396 B1 | 7/2001 | Dobrovolny | |
| 6,273,853 B1 | 8/2001 | Cartier et al. | |
| 6,296,609 B1 | 10/2001 | Brau | |
| 6,416,465 B2 | 7/2002 | Brau | |
| 6,537,212 B2 | 3/2003 | Sherts et al. | |
| 6,602,190 B2 | 8/2003 | Dobrovolny | |
| 6,648,818 B2 | 11/2003 | Cartier et al. | |
| 6,733,445 B2 | 5/2004 | Sherts et al. | |
| 6,763,775 B1 | 7/2004 | Sweeting | |
| 6,764,444 B2 | 7/2004 | Wu et al. | |
| 7,014,609 B2 | 3/2006 | Cartier et al. | |
| 7,052,457 B2 | 5/2006 | Fanous | |
| 7,156,805 B2 | 1/2007 | Thalgott et al. | |
| 7,166,113 B2 | 1/2007 | Arambula et al. | |
| 7,232,411 B2 | 6/2007 | Dinkler, II et al. | |
| 7,338,442 B2 | 3/2008 | Mulac et al. | |
| 7,435,219 B2 | 10/2008 | Kim | |
| 7,556,600 B2 | 7/2009 | Landry et al. | |
| 7,665,939 B1 | 2/2010 | Cardona | |
| 7,749,163 B2 | 7/2010 | Mulac et al. | |
| 7,811,230 B2 | 10/2010 | Hsueh et al. | |
| 8,100,827 B2 | 1/2012 | Farley | |
| 8,100,828 B2 | 1/2012 | Frey et al. | |
| 8,231,528 B1 | 7/2012 | Friedrich et al. | |
| 8,617,064 B2 | 12/2013 | Farley | |
| 8,894,029 B2 | 11/2014 | Agbodoe et al. | |
| 8,911,364 B2 | 12/2014 | Feigenwinter et al. | |
| 8,932,215 B2 | 1/2015 | Friedrich et al. | |
| 9,216,125 B2 | 12/2015 | Sklar | |
| 9,283,091 B2 | 3/2016 | Melkent et al. | |
| 9,320,506 B2 | 4/2016 | Bertagnoli et al. | |
| 9,427,328 B2 | 8/2016 | Drochner et al. | |
| 9,433,406 B2 | 9/2016 | Slagle et al. | |
| 9,549,723 B2 | 1/2017 | Hynes et al. | |
| 9,615,733 B2 | 4/2017 | Nottmeier | |
| 10,238,375 B2 | 3/2019 | O'Connell | |
| 2005/0080319 A1 | 4/2005 | Dinkler, II | |
| 2005/0171405 A1 | 8/2005 | Rowland et al. | |
| 2006/0149138 A1 | 7/2006 | Fanous | |
| 2006/0224044 A1 * | 10/2006 | Marchek | A61B 17/02 |
| | | | 600/233 |
| 2007/0038033 A1 | 2/2007 | Jones et al. | |
| 2007/0161867 A1 | 7/2007 | Fowler, Jr. et al. | |
| 2007/0208228 A1 | 9/2007 | Pavento et al. | |
| 2007/0235038 A1 | 10/2007 | Alinsod et al. | |
| 2007/0238933 A1 * | 10/2007 | Alinsod | A61B 17/02 |
| | | | 600/231 |
| 2009/0018401 A1 | 1/2009 | Kim | |
| 2010/0217271 A1 | 8/2010 | Pool et al. | |
| 2010/0274094 A1 | 10/2010 | Abdelgany et al. | |
| 2012/0130428 A1 | 5/2012 | Hunziker | |
| 2013/0019877 A1 | 1/2013 | Sklar | |
| 2013/0245383 A1 | 9/2013 | Friedrich | |
| 2014/0066718 A1 | 3/2014 | Fiechter | |
| 2014/0236234 A1 | 8/2014 | Kroll et al. | |
| 2014/0296918 A1 | 10/2014 | Fening et al. | |
| 2015/0100129 A1 | 4/2015 | Waugh et al. | |
| 2015/0265320 A1 | 9/2015 | Hynes et al. | |
| 2016/0008140 A1 | 1/2016 | Melkent et al. | |
| 2016/0081681 A1 | 3/2016 | Waugh et al. | |
| 2016/0081818 A1 | 3/2016 | Waugh et al. | |
| 2016/0089129 A1 | 3/2016 | Hennard et al. | |
| 2016/0095627 A1 | 4/2016 | Michelle | |
| 2016/0106553 A1 | 4/2016 | Melkent et al. | |
| 2016/0213489 A1 | 7/2016 | Drochner et al. | |
| 2016/0273676 A1 | 9/2016 | Junk | |
| 2017/0007227 A1 | 1/2017 | Hynes et al. | |

OTHER PUBLICATIONS

Written Opinion for PCT/US2017/017700, ISA, dated May 19, 2017, pp. 12.

\* cited by examiner

FIG. 8
FIG. 9
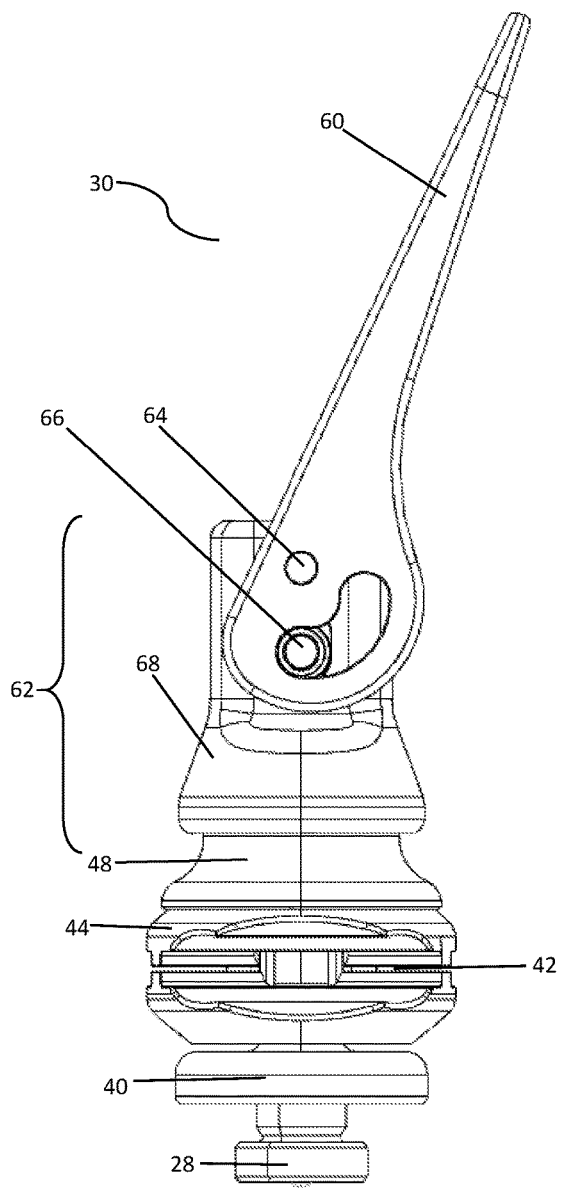
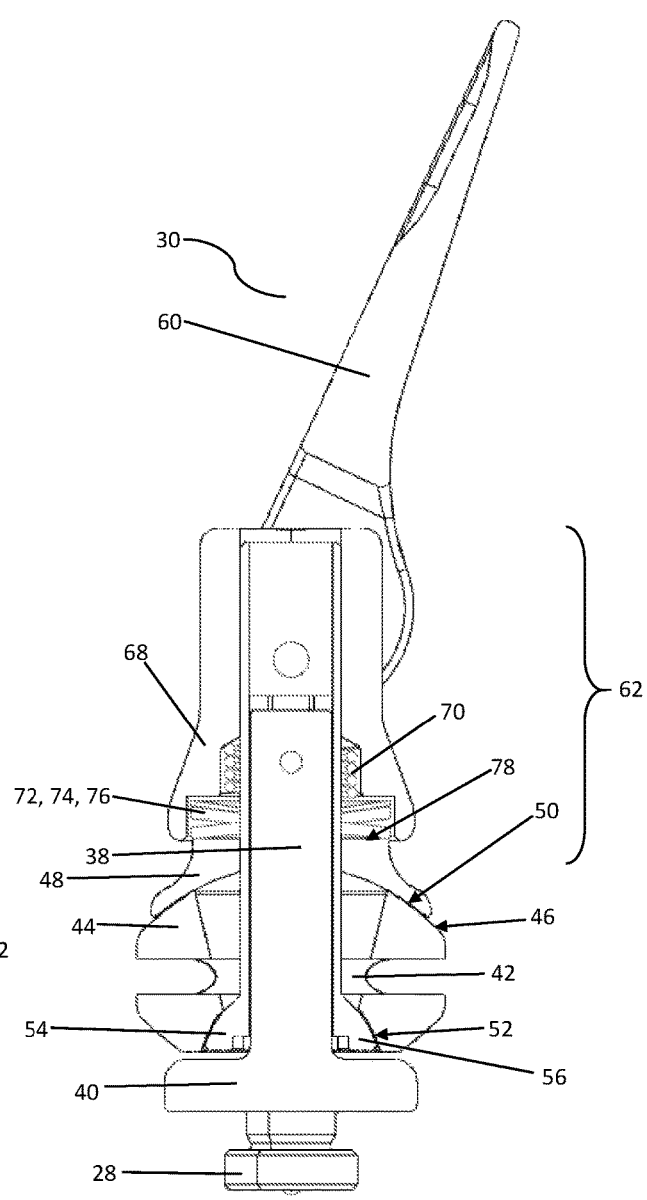

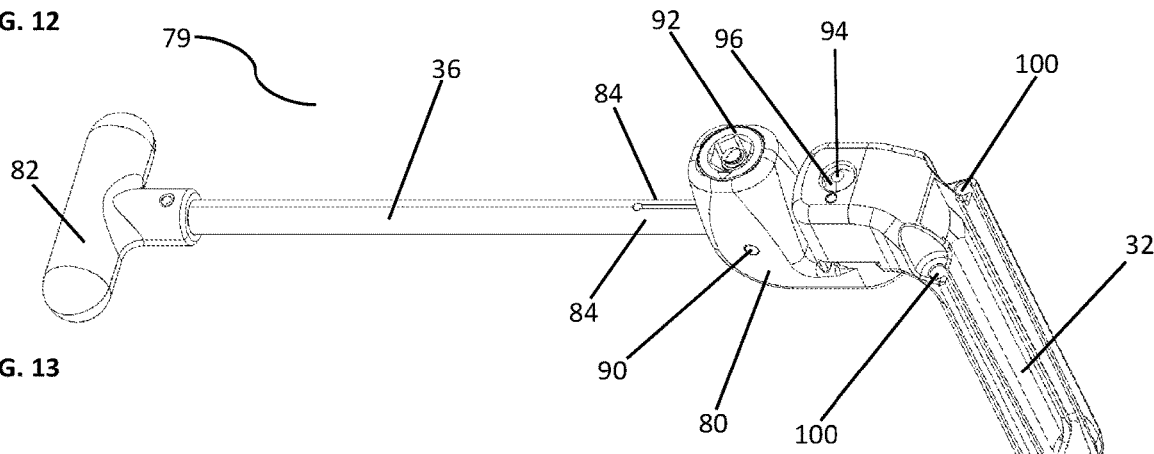
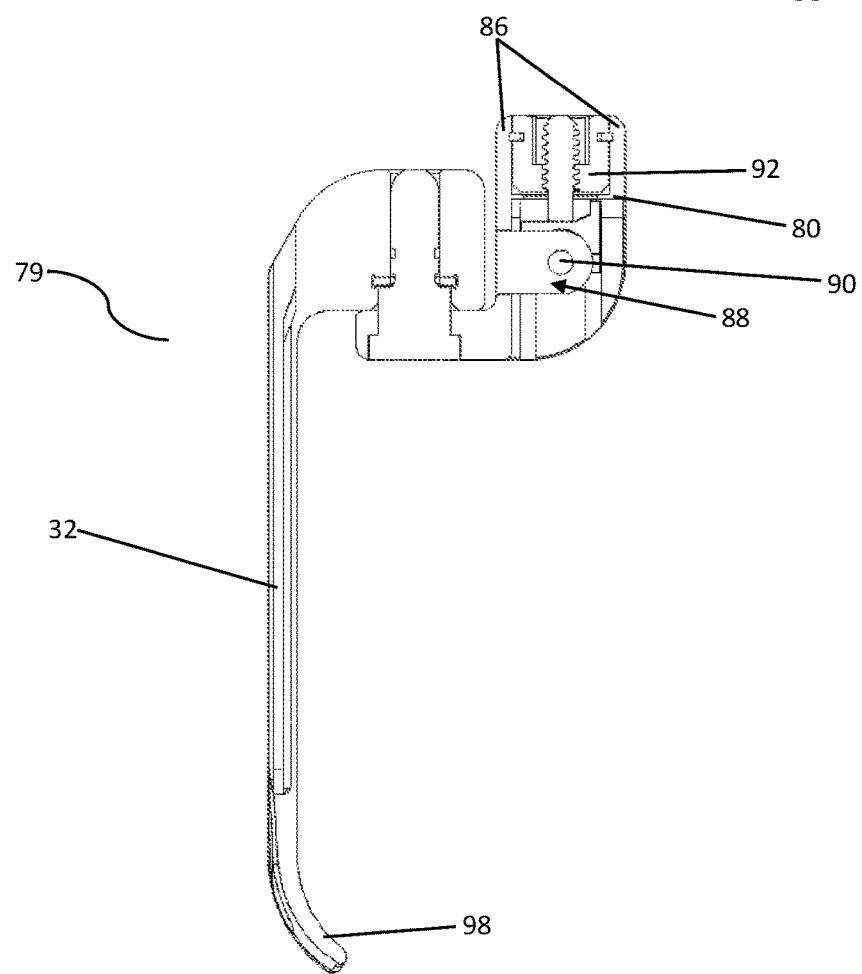

32

SURGICAL RETRACTOR

CROSS-REFERENCE TO RELATED APPLICATION

This application is a continuation of U.S. patent application Ser. No. 15/386,999 (currently pending), entitled "Surgical Retractor," and filed on Dec. 21, 2016, the entire contents of which is hereby expressly incorporated by reference into this disclosure as if set forth in its entirety herein.

BACKGROUND

Field

The present disclosure relates generally to medical devices, and specifically to surgical instruments and methods for performing spinal procedures.

Background

The spine is critical in human physiology for mobility, support, and balance. The spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination.

Fusion is one method of reducing the magnitude of the symptoms of damaged spinal discs, or for any pathology that would suggest direct spinal decompression as a treatment. The primary goals of fusion procedures are to provide stability between the vertebrae on either side of the damaged disc and to promote natural fusion of those adjacent vertebrae. Lumbar body interfusion is performed by three common methods: anterior lumbar interbody fusion (ALIF), posterior lumbar interbody fusion (PLIF), and transforaminal lumbar interbody fusion (TLIF). Generally, these procedures are performed through an "open" approach requiring a large incision and the separation and/or cutting of muscle and tissue, resulting in long recovery times and post-operative pain related to the procedure. To reduce the drawbacks associated with open procedures, less invasive techniques that reduce incision size and muscle cutting are becoming more popular. However, working through the smaller exposures brings other challenges, for example, decreased visualization and decreased flexibility in manipulating surgical instruments, among others, and thus the skill, training, and experience required for performing less invasive procedures is significantly higher than for open surgeries. A need therefore exists for improvements relating to the performance of minimally invasive procedures. The instruments and methods described herein are directed to addressing these needs.

SUMMARY

The present disclosure describes a retractor assembly, including parts thereof, useful for multiple less invasive approaches in spinal surgery. The retractor assembly can be used with a frame that can assume an open (arc or crescent) configuration or a closed, circular configuration. The modifiable nature of the frame confers flexibility to the retractor assembly in the types of procedures for which it can be used, and allows a surgeon to alter the configuration of the frame during a procedure as necessary. Retractor blades connect to the frame via a mobile carriage mounted in a groove track in the frame, in such a way as to confer six degrees of freedom of movement to the retractor blade. The blade itself pivots along a proximal/distal axis (yaws) and pivots along a first axis orthogonal to the proximal/distal axis (pitches) using independently lockable mechanisms.

In a first aspect, a retractor assembly for tissue retraction at the site of an incision is provided, the retractor assembly comprising: an arcuate frame member; a groove running along a proximal surface of the frame member; a mobile carriage engaged to the groove to allow the carriage to translate along the groove, the mobile carriage including a blade post holder attached to a blade post, and a carriage locking mechanism configured to allow the blade post six degrees of freedom of movement relative to the frame member when in an unlocked position, and to prohibit movement relative to the frame member when in a locked position except translation along the groove.

In a second aspect, a retractor assembly is provided comprising: an arcuate frame member having a first arc terminal end, a second arc terminal end, a first connector engagement feature at the first arc terminal end, and a second connector engagement feature at the second arc terminal end; an arcuate connector having a third arc terminal end, a fourth arc terminal end, a first frame engagement feature at the third arc terminal end configured to reversibly engage with the first connector engagement feature, and a second frame engagement feature at the fourth arc terminal end configured to reversibly engage with the second connector engagement feature; a groove running a long a proximal surface of the frame member; a mobile carriage engaged to the groove to allow the carriage to translate along the groove; and a retractor blade assembly comprising a retractor blade and a blade post engaged to the mobile carriage, and free to yaw, pitch, and roll relative to the mobile carriage.

In a third aspect, a mobile carriage for a retractor assembly is provided, comprising: a track engagement feature; a blade post holder configured to yaw, pitch, roll, and translate proximally and distally relative to the track engagement feature, the blade post holder having a post engagement feature configured to hold a cylindrical post such that the post is free to translate along the post's longitudinal axis relative to the blade post holder, and free to rotate about the post's longitudinal axis, but is otherwise constrained from moving relative to the blade post holder; a carriage locking mechanism in contact with the blade post holder, configured to reversibly exert compressive force on the blade post holder to inhibit the blade post holder from yaw, pitch, and roll relative to the track engagement feature, wherein such compressive force causes the post engagement feature to exert compressive force on the cylindrical post to restrict the post from translating along the post's longitudinal axis.

In a fourth aspect, a mobile carriage for a retractor assembly is provided, comprising: a track engagement feature; a base that does not translate relative to the track engagement feature; a column extending from the base in a proximal direction, and that does not translate relative to the base; a collar element having an elongate proximal portion and a partially ellipsoidal distal flared portion, said collar element at least partially surrounding the column; an articulating post holder having a concave distal surface that forms a ball joint with the partially ellipsoidal distal flared portion of the collar element, a horizontal post channel, a partially ellipsoidal proximal surface, and an aperture through which the column extends; and a locking mechanism having a concave distal surface in contact with the partially ellipsoidal proximal surface of the articulating post holder, and a manual compression switch to exert distally vectored compressive force on the proximal surface of the articulating post holder, which in turn exerts distally vectored compressive force on the collar element, to restrict movement of the collar element relative to the column, to restrict movement of the post holder relative to the column, and to restrict movement of the post in the post channel.

In a fifth aspect, a retractor blade is provided comprising: a blade holder attached to a blade post, and which pitches relative to the blade post; a first locking mechanism configured to arrest pitch of the blade holder relative to the blade post; a retractor blade rotatably engaged to the blade holder to allow the blade to yaw relative to the blade holder; and a second locking mechanism configured to arrest yaw of the retractor blade relative to the blade holder independent of the first locking mechanism.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 8. A side view of the carriage member of the retractor assembly of FIG. 1 in an unlocked position.

FIG. 9. A cutaway of the carriage member shown in FIG. 8.

FIG. 12. A perspective view of the retractor blade and retractor blade post shown in FIG. 1.

FIG. 13. A side cutaway view of the retractor blade shown in FIG. 1.

DETAILED DESCRIPTION

Illustrative embodiments of a surgical retractor assembly are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The retractor assembly disclosed herein boasts a variety of inventive features and components that warrant patent protection, both individually and in combination.

The overall configuration of an illustrative embodiment of the retractor assembly 2 is shown in FIGS. 1-4. In that embodiment, an arcuate frame 4 extends around an arc of about 270°. An arcuate connector member 6 extends around an arc of about 90°, completing the circle when engaged to the frame member 4. In this context "arcuate" means that both the frame member 4 and the connector member 6 have a general shape of an arc of a circle; the arc may in some embodiments depart from the arc of a circle, for example either may be an arc of an ellipse or an oval. The frame member 4 defines an arc of less than 360°, leaving an opening sufficiently wide to allow surgical instruments to be deployed through the opening into a retracted incision. Some embodiments of the frame member 4 define an arc of less than 315°. Further embodiments define an arc of 315, 300, 285, 270, 255, 240, 225, 210, 195, 180, 165, 150, 135, 120, 105, 90, 75, 60, 45, 30, or 15°.

Figure 1:
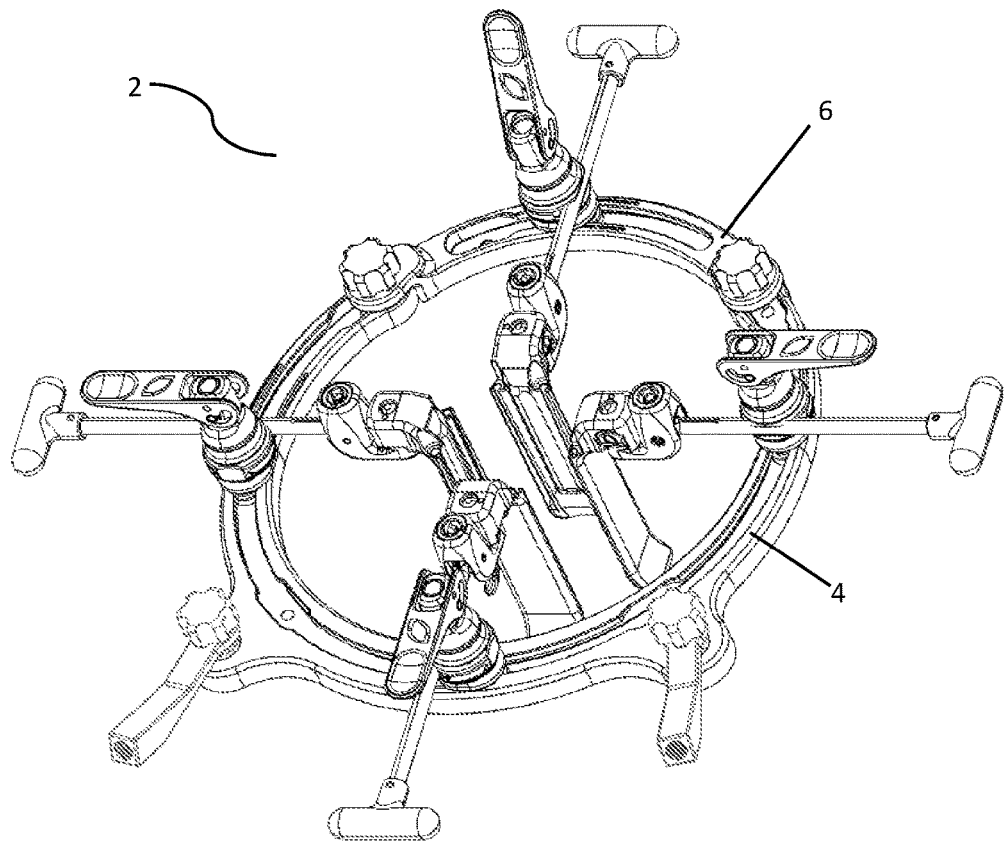
FIG. 1. A perspective view of an embodiment of the retractor assembly.
Figure 2:
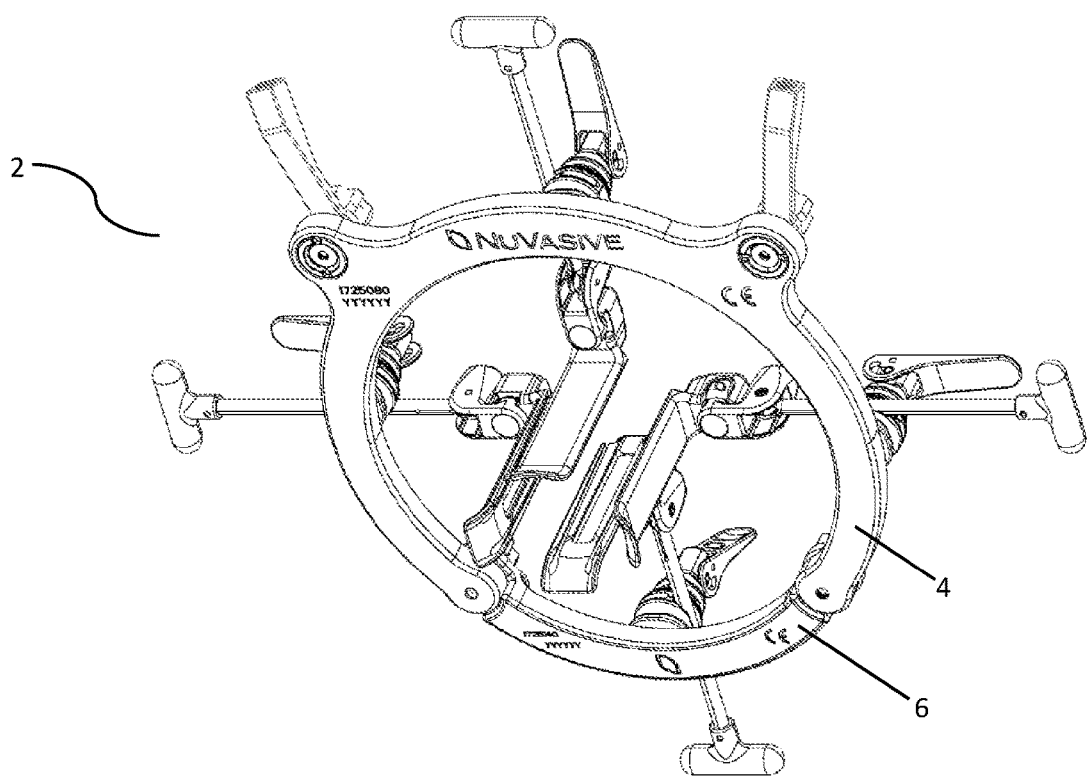
FIG. 2. An alternative perspective view of the embodiment of the retractor assembly of FIG. 1.
Figure 3:
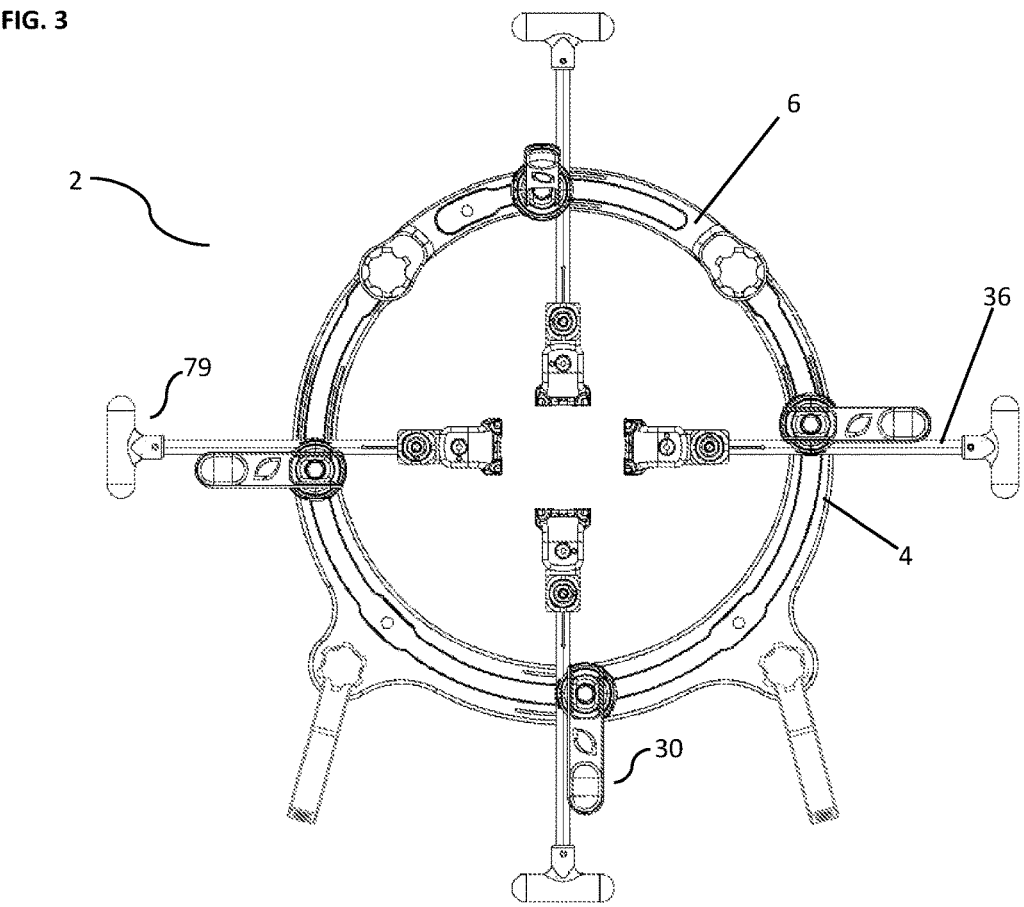
FIG. 3. A top view of the embodiment of the retractor assembly of FIG. 1.
Figure 4:
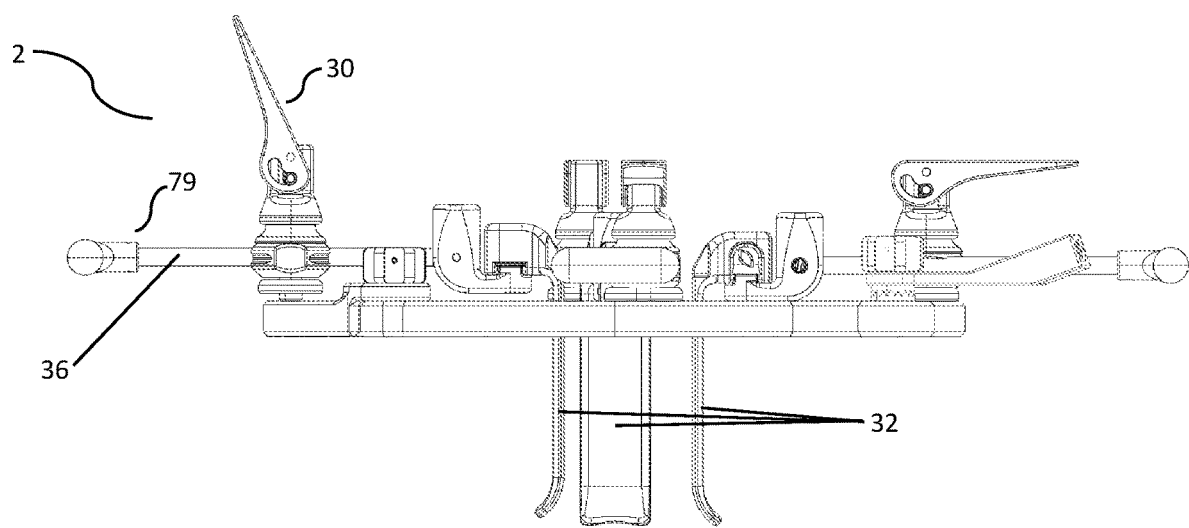
FIG. 4. A side view of the embodiment of the retractor assembly of FIG. 1.
Figure 5:
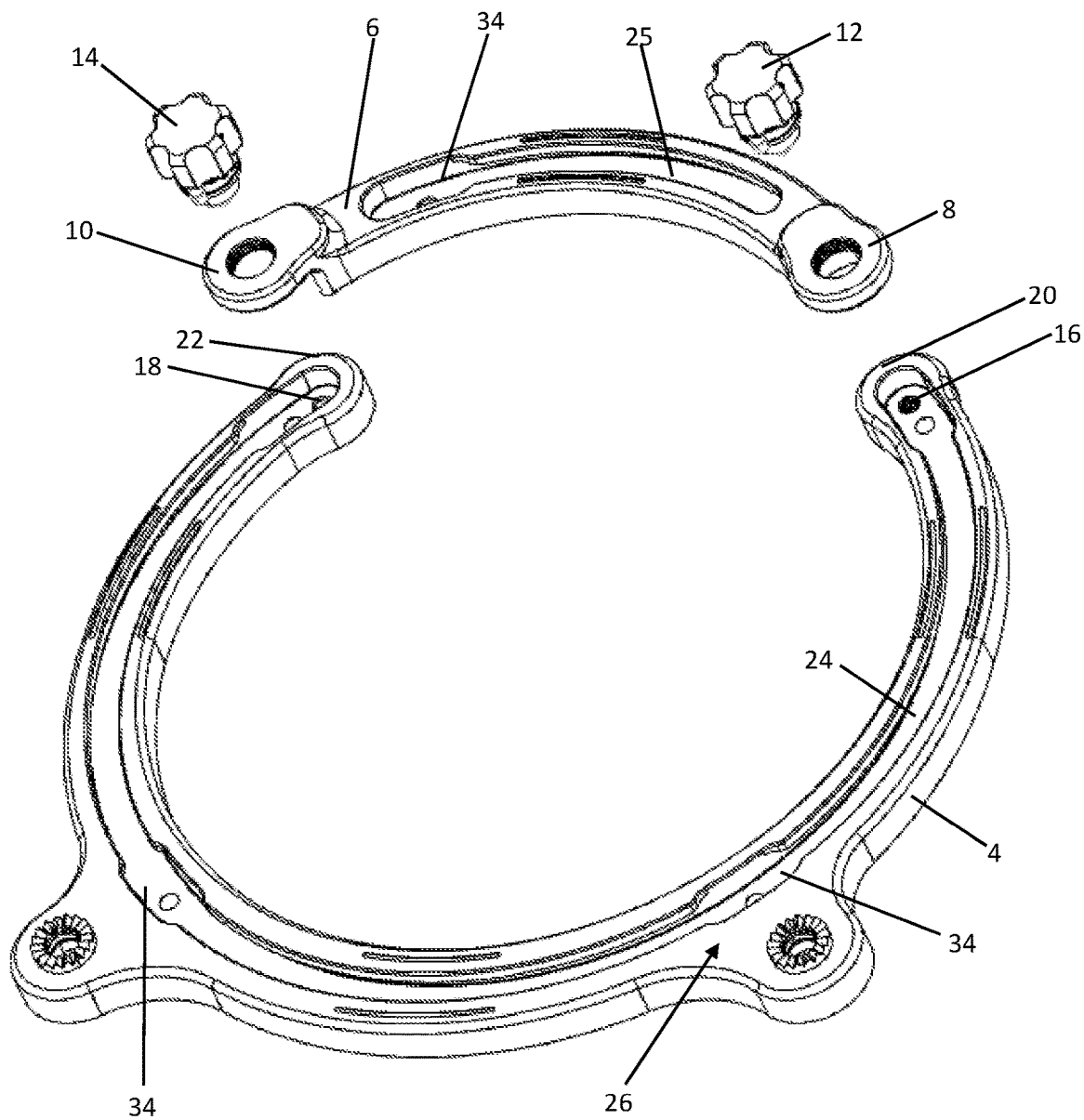
FIG. 5. An exploded perspective view of the frame member and connector member of the retractor assembly of FIG. 1.

The arcuate connector member 6 defines an arc as described above, which complements the arc of the frame member 4 to complete the circle (ellipse, oval, etc.). The connector member 6 also has terminal ends of the arc, referred to herein as a third arc terminal end 8 and a fourth arc terminal end 10 (FIG. 5). The connector member 6 comprises a first frame engagement feature 12 and a second frame engagement feature 14 at the third and fourth arc terminal ends 8 and 10, respectively. The frame engagement features 12 and 14 are either fasteners or features for receiving fasteners. In some embodiments of the arcuate connector the frame engagement features are part of a quick-connect mechanism. In the illustrated embodiment, the frame engagement features 12 and 14 are thumb screws. The frame member 4 also has a first connector engagement feature 16 and a second connector engagement feature 18 at a first terminal arc end 20 and a second terminal arc end 22, respectively, which likewise may be fasteners or features for receiving fasteners (such as complementary parts of a quick-connect mechanism). In the illustrated embodiment, the frame member 4 comprises threaded passages to accept the thumb screws.

Figure 6:
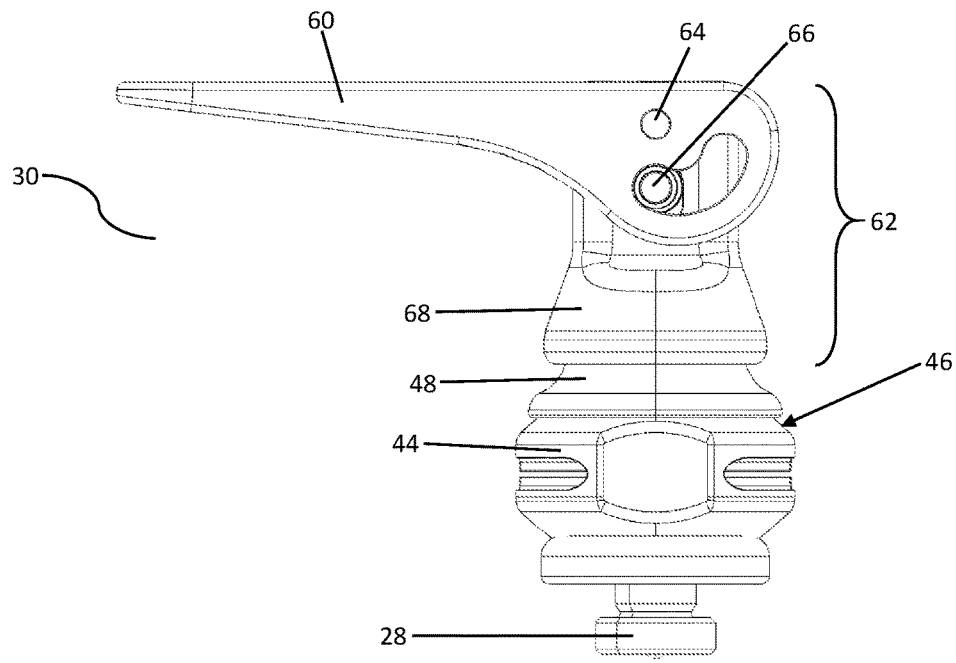
FIG. 6. A side view of the carriage member of the retractor assembly of FIG. 1 in a locked position.

The frame member 4 comprises a first groove 24 running along a proximal surface 26 of the frame member 4. The first groove 24 may run from the first arc terminal end 20 to the second arc terminal end 22, as in the illustrated embodiment, or it may run over a subset of that distance. The connector member 6 may comprise a second groove 25 running parallel to the proximal surface 26. The second groove 25 may run from the third arc terminal end 8 to the fourth arc terminal end 10. Some embodiments of the frame member 4 and the connector member 6 may have more than one groove 24 covering subsets of the distance from the first terminal end 20 to the second terminal end 22, and the third arc terminal end 8 to the fourth arc terminal end 10 (in effect an interrupted groove). Each groove 24 and 25 is structured to accept a track engagement feature 28 from a carriage 30, as shown (FIGS. 6, 8, and 9). Some versions of the groove are configured to allow the carriage to translate along the groove, while constraining the carriage from departing from the groove. In a specific embodiment, the cross-sectional profile of the grooves 24 and 25 has a narrow proximal neck and a broader distal foot (not shown). This may take the form of the grooves 24 and 25 having a cross-sectional profile of an inverted letter T, in which the stem of the T intersects the proximal surface 26 of the frame member 4. The track engagement feature 28 could engage the first groove 24 or the second groove 25 by having a complementary shape, i.e. a narrow stem and a broad base resembling an inverted T. Such a configuration would allow the carriage 30 to translate along the grooves 24 and 25, but would constrain the carriage 30 from leaving the grooves 24 and 25. Other shapes are of course possible, such as a keyhole shape and a triangular shape.

Figure 10:
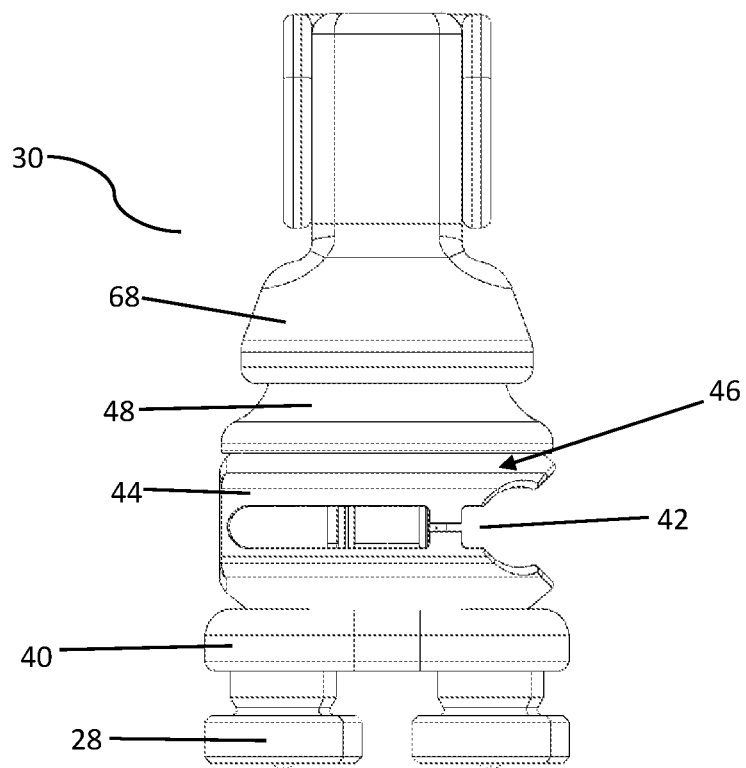
FIG. 10. A front view of the carriage member of the retractor assembly of FIG. 1, with the thumb switch omitted to reveal detail.
Figure 11:
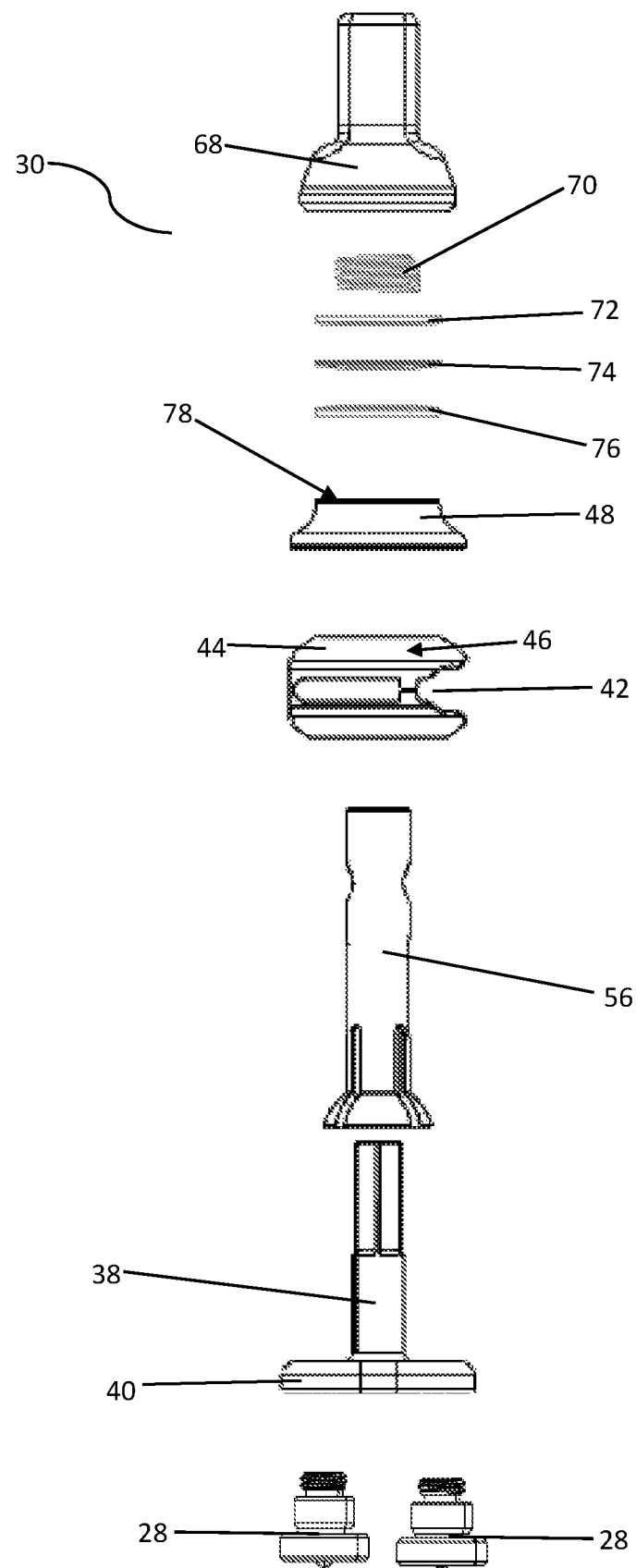
FIG. 11. A front exploded view of the carriage member shown in FIG. 10 showing detail of the locking mechanism therein.
Figure 14:
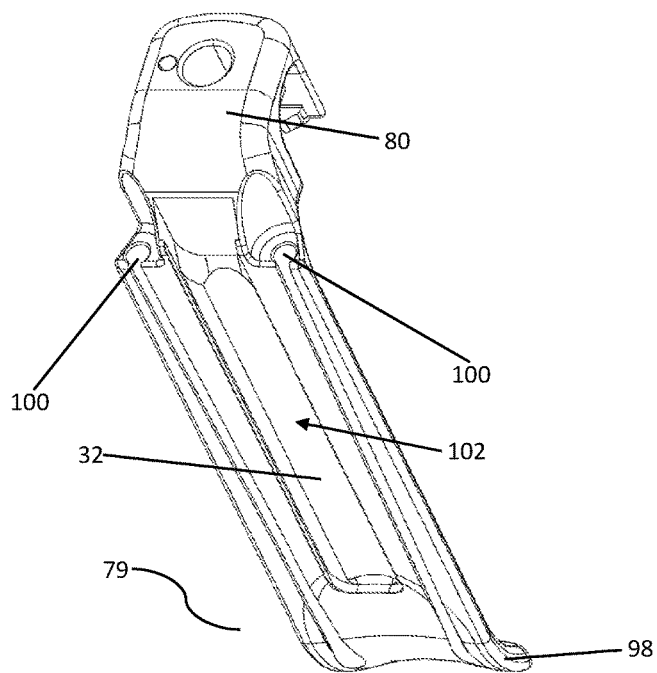
FIG. 14. A perspective view of the retractor blade shown in FIG. 1, showing the inner surface with anchor channels.
Figure 15:
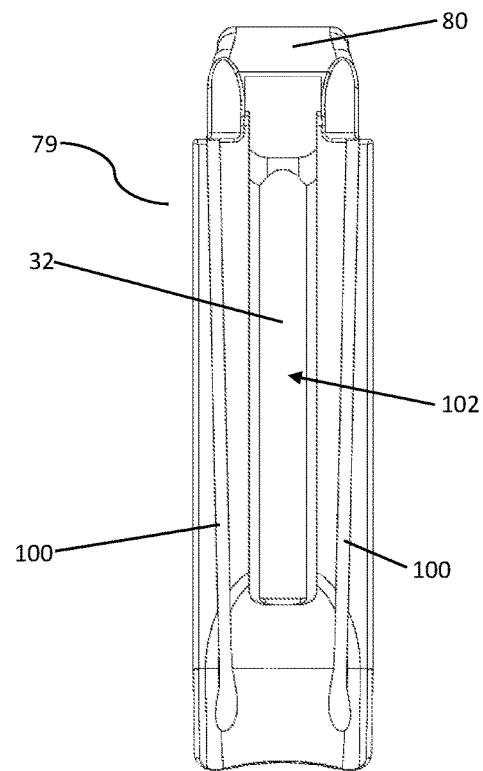
FIG. 15. A front view of the retractor blade shown in FIG. 1, illustrating the convergence of the anchor channels.

FIG. 10 shows a specific embodiment of the track engagement feature 28 on the carriage 30 that is suitable for use in the grooves 24 and 25 that has the inverted T shape discussed above. The use of the two track engagement features 28 in static relationship to one another results in the carriage 30 translating along the grooves 24 and 25 and simultaneously yawing so that the same side of the carriage 30 always faces the center of the circle defined by the frame member 4. Assuming that the incision is approximately in the center of the circle defined by the frame member 4, such a configuration has the advantage of keeping a retractor blade 32 oriented toward the incision while the carriage 30 translates along the first groove 24 or the second groove 25.

Additional features may be present in the grooves 24 and 25 to facilitate the easy insertion and removal of the carriages 30. As shown in FIG. 5, the grooves 24 and 25 may contain an expanded portion 34 that is wider than the foot of the track engagement feature 28. Thus the carriage 30 can be dropped into the expanded portion 34 and slid into the narrower portion of the grooves 24 and 25, from which it cannot be removed. As in FIG. 5, a given groove 24 and 25 may have multiple expanded portions 34, as shown in the first groove 24 in the frame member 4. A given groove 24 and 25 might have only one expanded portion 34 also, as shown in the second groove 25 of the connector member 6.

Figure 7:
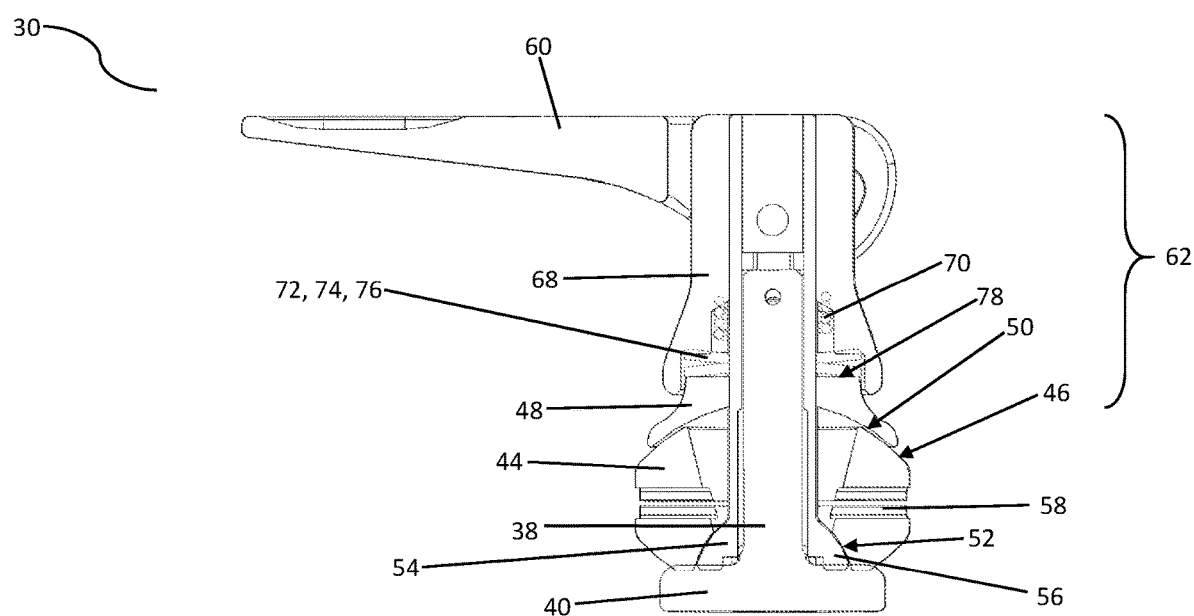
FIG. 7. A cutaway of the carriage member shown in FIG. 6.

The carriage 30 functions to connect the retractor blade 32 to the frame member 4 or the connector member 6 via a blade post 36 on which the retractor blade 32 is mounted. The carriage 30 translates through the grooves 24 and 25 while allowing the blade post's 36 orientation to be varied while the carriage 30 is unlocked. The embodiments of the carriage 30 shown in the accompanying drawings allow the blade post 36 to move with six degrees of freedom (translation in three dimensions as well as yaw, pitch, and roll rotational motion). For the purposes of this discussion, yaw refers to rotation about the distal/proximal axis of the carriage; pitch refers to rotation about an axis parallel to a tangent to the frame member 4 at the location of the carriage 30; and roll refers to rotation about an axis that intersects the frame member 4 at the location of the carriage 30 and the center of the circle generally defined by the frame member 4. The illustrated embodiment shows the carriage 30 configured for translation along the grooves 24 and 25, as explained above. This configuration also allows translation along the distal/proximal axis. As shown in FIGS. 7 and 9, the carriage 30 contains a column 38 affixed to a base 40 that allows the rest of the carriage 30 to translate distally and proximally unless and until the carriage 30 is locked. The blade post 36 translates along its own longitudinal axis by moving back and forth in a post channel 42 (best shown in FIG. 10), which can also be locked.

The carriage 30 has a blade post holder 44 that can yaw, pitch, and roll when unlocked. An embodiment of the blade post holder 44 is shown in FIGS. 6-9 and 11. Best shown in FIG. 11, the illustrated embodiment comprises an articulating blade post holder 44 with a partially ellipsoidal proximal surface 46. In this context "partially ellipsoidal" means that part of the surface defines the surface of an ellipsoid; similarly, "partially spherical" means that part of the surface defines the surface of a sphere. In the embodiment shown, the proximal surface 46 of the articulating blade post holder 44 is partially spherical, and forms a ball joint connected with a post holder compressing body 48. The post holder compressing body 48 has a complementary distal surface 50 that mates with the proximal surface 46 of the post holder 44 (shown in FIGS. 7 and 9). These surfaces 50 and 46 may be roughened to allow them to articulate relative to one another when not under any compression, but to be firmly locked into position when under compression. The post holder 44 has a concavity 52 in its distal surface 50 (shown in FIGS. 7 and 9) that is also partially ellipsoidal (partially spherical as shown). The concavity 52 in the distal surface of the post holder 44 mates with a complementary flared portion 54 on the distal end of a collar member 56. Again, a ball joint is formed, allowing articulation of the post holder 44 in any direction relative to the collar member 56. Furthermore, the post channel 42 shown in FIGS. 10-11 allows the cylindrical post 36 to rotate about its own longitudinal axis.

The blade post 36 is locked in position relative to the carriage 30 when compressive force with a distal vector is exerted by the post holder compressing body 48 on the proximal surface 46 of the post holder 44. The direct effect is to prevent the post holder 44 from deflecting relative to the post holder compressing body 48. It also causes the post holder 44 to pinch the post channel 42, holding it in place and preventing it from translating along its longitudinal axis. Note that in the illustrated embodiment, the post holder 44 is deeply notched to facilitate flexing, and also has a pair of stop features 58 to prevent over-compression. The post holder 44 in turn exerts distally vectored compressive force on the flared portion 54 of the collar member 56. Not only does this arrest deflection of the post holder 44 relative to the collar member 56, but it causes the collar member 56 to squeeze the column 38 that it surrounds. Be exerting radially vectored compressive force on the column 38, the collar member 56 arrests the translation of the post holder 44 in the proximal/distal direction. The compressive force may also arrest the translation of the carriage 30 along the grooves 25 and 25 in some embodiments of the retractor assembly 2, although in the illustrated embodiment it does not.

In short, the mechanism shown in the figures harnesses distally vectored compressive force on the proximal surface 46 of the post holder 44 to arrest all movement of the blade post 36 relative to the carriage 30; and all movement relative to the frame member 4 and the connector member 6, except to translate along the grooves 24 and 25 with the carriage 30.

Compression may be imparted to the proximal surface 46 of the post holder 44 using a manual switch 60, numerous of which are known in the art. A particular embodiment of a locking mechanism 62 is shown in detail in FIGS. 6-9 and 11. The manual switch 60, which may be a thumb switch, rotates around a pivot 64 and rotates a cam 66 that pushes a compressive body 68 in the distal direction. The compressive body 68 is capable of translation in the proximal/distal directions relative to the column 38, the base 40, and the collar member 56. The compressive body 68 exerts distally vectored compressive force on a spring 70 (which is outwardly biased) and simultaneously on one or more compression washers; a specific embodiment of the carriage contains three compression washers (that is, a first compression washer 72, a second compression washer 74, and a third compression washer 76). The spring 70 provides some resistance and allows the thumb switch 60 to return to its original position easily when it is unlocked. The washers 72, 74 and 76 sit on a proximal surface 78 of the post holder compressing body 48, and transfer compressive force from the compressing body 48 to the post holder 44. The compressive force thus imparted to the blade post holder 44 locks the post 36 and the post holder 44 in position as described above.

An embodiment of a retractor blade assembly 79 is shown in FIGS. 12-15. The blade assembly 79 is shown mounted on the cylindrical blade post 36 via a blade holder 80. The blade post 36 is connected to a blade post handle 82 that allows the blade post 36 to be manually translated along its own longitudinal axis and to be manually rotated around its own longitudinal axis ("roll"). The blade assembly 79 does not translate relative to the blade post 36, but is configured to pitch and yaw relative to the blade post 36. In the context of this discussion of the retractor blade assembly 79, rotation around the longitudinal axis of the blade post 36 is "roll;" rotation around a distal/proximal axis that is orthogonal to the longitudinal axis of the blade post is "yaw;" and rotation around the axis that is orthogonal to both of the foregoing axes is "pitch."

The illustrated retractor blade assembly 79 has mechanisms that independently lock the pitch and yaw of the blade 32 relative to the blade post 36. As shown in FIG. 12, the blade post 36 divides into two arms 84 at the end attached to the blade holder 80. The two arms 84 of the post 36 terminate in disc-shaped clamping elements 86, each having a central aperture (not shown), and the axis of the discs 86 being orthogonal to the longitudinal axis of the blade post 36. The discs 86 each have an internal surface facing the other disc 86. An axle 90 runs through the apertures in the discs. Between the discs 86 is a disc compression surface 88 that is immobile relative to the blade holder 80 (the disc compression surface also has a central aperture for the axle 90). In a configuration in which the blade assembly 79 is unlocked as regards pitch, the discs 86 do not exert compression on the disc compression surface 88, and so there is little or no friction between them, which allows the blade assembly 79 to pitch relative to the blade post 36 around the axle 90. However, in a locked configuration, the discs 86 converge to pinch the disc compression surface 88, which arrests pitch. The locking effect can be improved if the internal surfaces of the discs 86 are scalloped (like poker chips) and both sides of the compression surface 88 are scalloped in a complementary fashion. In the illustrated embodiment, the discs 86 are caused to pinch the disc compression surface 88 by rotation of a locking nut 92 on the proximal side of the blade assembly 79, a process that can of course be reversed by rotation of the locking nut 92 in the opposite direction.

The retractor blade assembly 79 in the illustrated embodiment yaws relative to the blade post 36 around a pole 94 that extends in the proximal/distal axis. It has a locking mechanism 96 that arrests yaw that is independent of the pitch locking nut 92.

The retractor blade 32 itself may be of any configuration that is known to be suitable in the art. In the illustrated embodiment, the retractor blade 32 is substantially vertical (i.e., extends in the proximal/distal axis) with a distal curved portion 98 that curves back toward the frame member 4. The blade 32 can be used while it is anchored to a physiological structure, such as a bone (not shown). The anchor (such as a bone anchor—not shown) is secured to the retractor blade 32 shown in the figures via two anchor channels 100. Note that the anchor channels 100 converge slightly in the distal direction, which increases the stability of the blade 32 while anchored using two anchors. The location of the anchor channels 100 on an inner face 102 of the retractor blade 32 that faces away from the nearest portion of the frame member 4 ("inner face") serves to prevent the anchors from contacting unintended physiological structures outside of the incision. For example, when the spine is accessed via an anterior approach, the retractor blades 32 are placed between the common iliac vessels. When bone anchors are used at the tips of the retractor blades 32 this creates a risk that the anchors may contact one or more of the common iliac vessels. Embodiments of the retractor blade 32 in which the anchor channels 100 are located on the inner face 102 of the blade 32 have the advantage of shielding the common iliac vessels from contact with the bone anchors. A method of providing retraction during an anterior approach to a lumbar or sacral vertebra involving inserting any of the retractor blades 32 above is thus provided, comprising inserting a bone anchor into the anchor channel 100, and anchoring the retractor blade 32 to the lumbar or sacral vertebra by the bone anchor.

Surgical procedures are provided employing the retractor assembly 2, comprising inserting one or more of the retractor blades 32 into an incision, and securing the retractor blade 32 to the frame member 4 before, during, or after insertion. One example of such a procedure is an anterior approach to the spine. The anterior approach can be used to access the lower spine, such as the lumbar or sacral region, with the patient either in the supine or lateral decubitus position.

Figure 16:
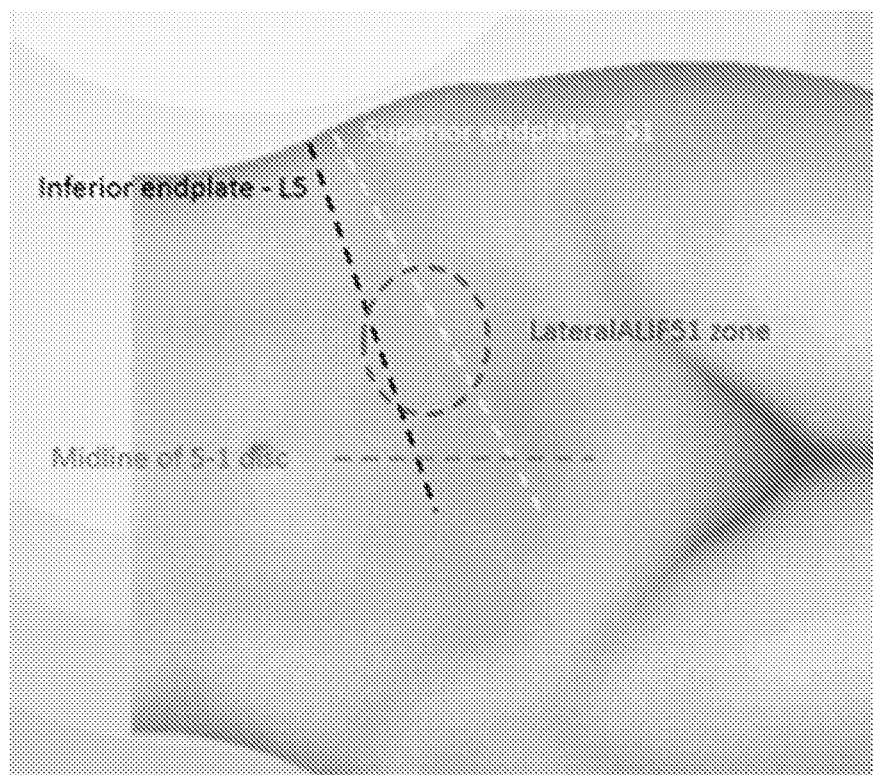
FIG. 16. An anterior view of a patient in the lateral decubitus position showing anatomic landmarks for the initial incision of an exemplary embodiment of the surgical method.
Figure 17:
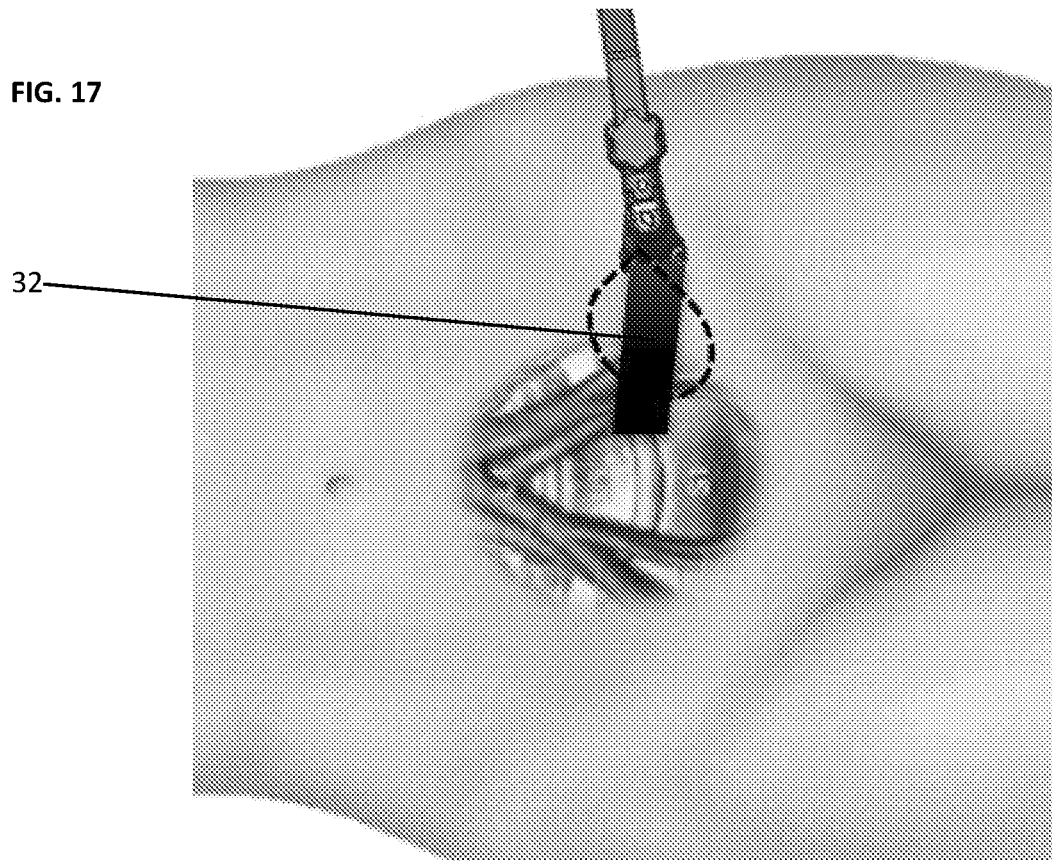
FIG. 17. An anterior view of the placement of a lateral retractor blade once a pathway to the disc space has been cleared according to the same embodiment of the method as in FIG. 16.

By way of example, a method of accessing the anterior lumbar spine is provided, while the patient is in the lateral decubitus position. The patient is placed in lateral decubitus with a slight anterior tilt, left side up with the legs straight. Following standard surgical preparation, the disc space is localized using lateral fluoroscopy. A template is used to make skin markings to define the iliac crest, inferior endplate of L5, superior endplate of S1 (FIG. 16). Next, a midline mark is made on the skin. An oblique incision is made lateral to the rectus and cephalad to the inguinal ligament and an alternating blunt scissor and finger dissection is used to enter the retroperitoneal space. Once the index finger is inside the space, a gentle sweeping motion is used to palpate the left common iliac vessels and create a space through which a first retractor blade 32 may pass. The initial retractor will first pass through the retroperitoneal space and dock on the disc just medial to the common iliac vessels. Once a pathway to the disc space is created, the first (lateral) blade 32 is placed medial to the descending common iliac vessels and lateral to the disc space (FIG. 17). The approximate incision location noted with black dotted line. Once the lighted retractor is in place, the retractor blade 32 is anchored by placement of the initial bone anchor into the 51 vertebral body.

Figure 18:
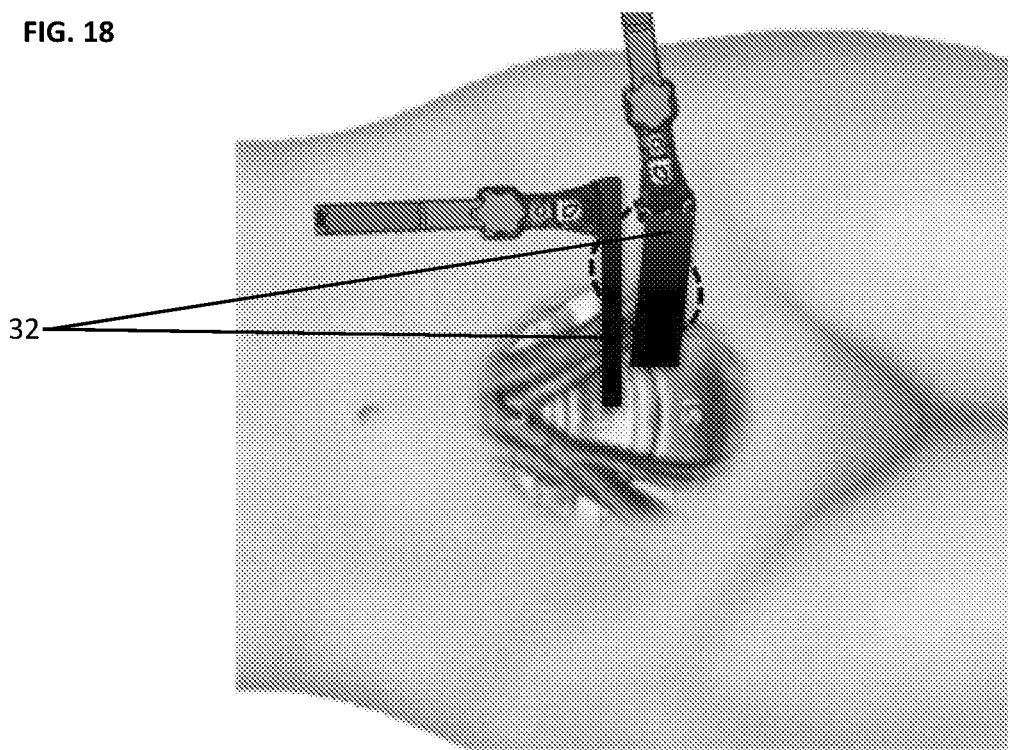
FIG. 18. An anterior view of the placement of a cranial retractor blade after placement of the lateral blade according to the same embodiment of the method as in FIGS. 16-17.
Figure 19:
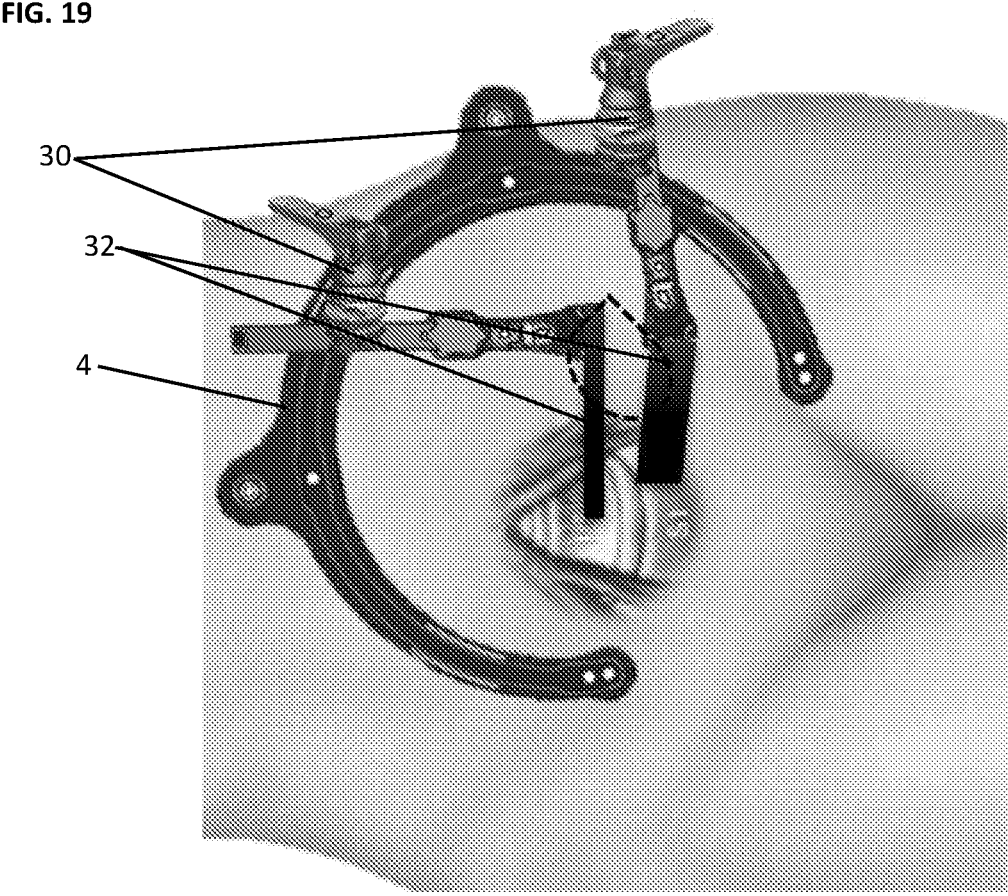
FIG. 19. An anterior view of the placement of an embodiment of the frame member after placement of the lateral and cranial blades according to the same embodiment of the method as in FIGS. 16-18.
Figure 20:
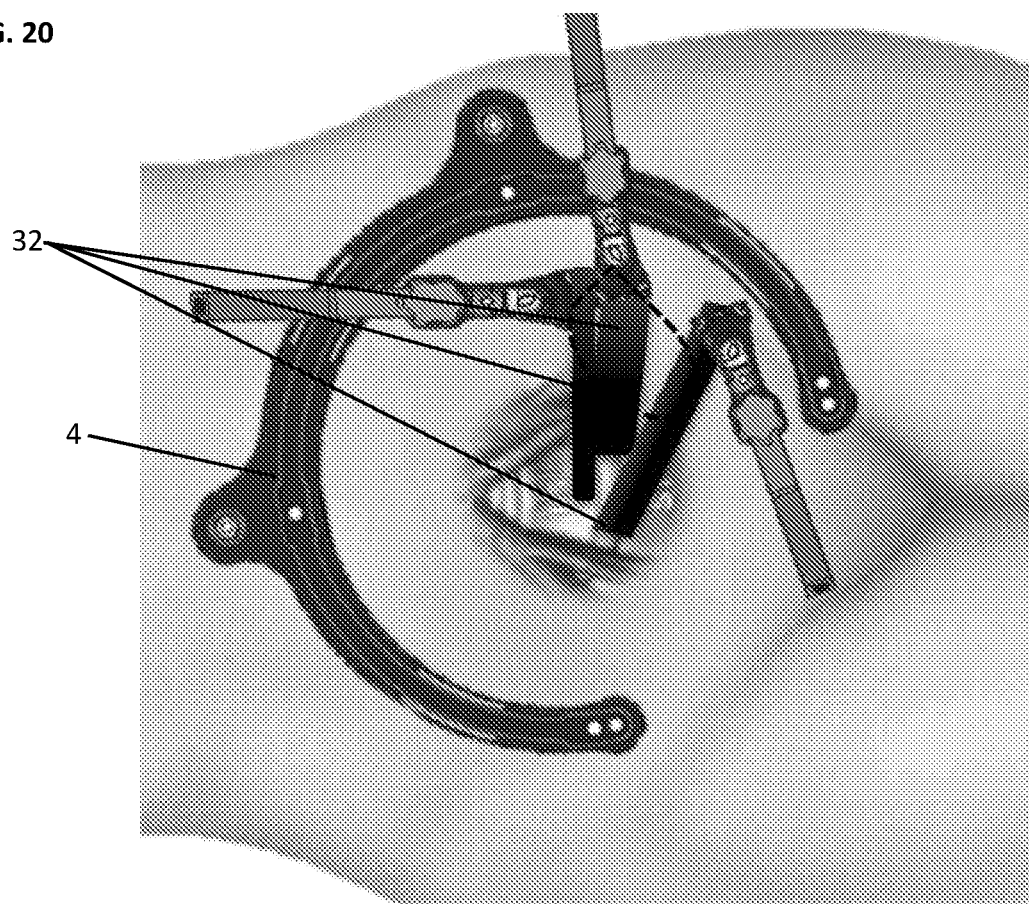
FIG. 20. An anterior view of the placement of an embodiment of a medial blade after placement of the lateral and cranial blades on the frame member according to the same embodiment of the method as in FIGS. 16-19.

As shown in FIG. 18, a second (cranial) retractor blade 32 may be guided down the superior aspect of the disc space and below the descending vessel bifurcation, and anchored to the L5 vertebral body by means of a bone anchor. The frame member 4, comprising two or more carriages 30, can be positioned posterior to the incision as shown in FIG. 19. The frame member 4 may be supported by any suitable means, such as by a C-arm. In the illustrated embodiment of the method, the frame member 4 is approximately centered over the incision. Note the open arc (approximately 270°) formed by the illustrated embodiment of the frame member 4, which provides more flexibility with spinal instrumentation during discectomy and implant placement when the patient is in lateral decubitus. As shown in FIG. 20, a third (medial) retractor blade 32 may then be positioned in the incision, and either held manually or secured to the frame member 4 using another carriage 30.

In lateral decubitus no fourth blade 32 may be necessary, as the contents of the abdominal cavity have a tendency to fall away from the accessed region of the lumbar spine under the force of gravity. Thus the frame member 4 need not include the connector member 6 (although under some circumstances the connector member could be used to provide additional retraction). When the procedure is performed in the supine position, the connector member 6 may be emplaced, and one or more additional carriages 30 may be inserted into the second groove 25 on the connector member to support one or more additional retractor blades 32.

Once access to the lumbar spine has been achieved, any of various procedures may be performed. In a specific embodiment of the method a lumbar interbody fusion procedure is performed while the retractor assembly 2 is in place.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

The following is claimed:

1. A retractor assembly for tissue retraction at the site of an incision, the retractor assembly comprising:
    an arcuate frame member that extends around an arc;
    a groove running along a proximal surface of the frame member;
    a mobile carriage engaged to the groove to allow the carriage to translate along the groove, the mobile carriage including:
    a blade post holder attached to a blade post; and
    a single carriage locking mechanism configure to allow the blade post six degrees of freedom of movement relative to the frame member when in an unlocked position, and to prohibit movement relative to the frame member when in a locked position except translation along the groove.

2. The retractor assembly of claim 1, wherein the carriage locking mechanism is configured to exert compressive force on the blade post holder to inhibit the blade post holder from translating proximally and distally.

3. The retractor assembly of claim 1, wherein the carriage locking mechanism comprises a manual switch that that confers compressive force via a flexible body capable of storing compressive energy interposed between the manual switch and the post holder.

4. The retractor assembly of claim 1, wherein the carriage locking mechanism comprises a thumb switch coupled to a cam that confers compressive force via a spring and a plurality of washers interposed between the thumb switch and the post holder.

5. The retractor assembly of claim 1, wherein the blade holder is configured to pitch relative to the blade post, wherein the blade holder comprises:
    a first locking mechanism configured to arrest pitch of the blade holder relative to the blade post;
    a retractor blade rotatably engaged to the blade holder to allow the blade to yaw relative to the blade holder; and
    a second locking mechanism configured to arrest yaw of the retractor blade relative to the blade holder independent of the first locking mechanism.

6. The retractor assembly of claim 5, wherein the blade post is split into two post arms terminating in a part of parallel disc members, each disc member containing a central aperture, and each disc member having a scalloped surface facing the other disc member;
    the blade holder comprising:
    a compression body between the pair of disc members, having a second central aperture and having at least two surfaces each proximate to one of the pair of disc members, the at least two surfaces having scalloped textures that interlock with the scalloped surfaces on the disc members;

an axle running through the apertures on the disc members and the second aperture in the compression body; and a locking mechanism that reversibly pinches the pair of disc members against the compression body to arrest pitch of the blade holder relative to the blade post.

7. The retractor assembly of claim 1, further comprising:
at least a second mobile carriage configured to initially engage with the groove and subsequent to an initial engagement, engage with the groove to allow the second mobile carriage to translate along the groove.

8. The retractor assembly of claim 1, further comprising:
a retractor blade assembly coupled to the blade post, wherein the retractor blade assembly includes a retractor blade.

9. A retractor assembly for tissue retraction at the site of an incision that can be used in an open or closed configuration, the retractor assembly comprising:
an arcuate frame member that extends around an arc and having a first arc terminal end, a second arc terminal end, a first connector engagement feature at the first arc terminal end, and a second connector engagement feature at the second arc terminal end;
an arcuate connector having a third arc terminal end, a fourth arc terminal end, a first frame engagement feature at the third arc terminal end configured to reversibly engage with the first connector engagement feature, and a second frame engagement feature at the fourth arc terminal end configured to reversibly engage with the second connector engagement feature;
a groove running along a proximal surface of the frame member;
a mobile carriage engaged to the groove to allow the carriage to translate along the groove;
a retractor blade assembly comprising a retractor blade and a blade post engaged to the mobile carriage, and free to yaw, pitch, and roll relative to the mobile carriage; and
a single carriage locking mechanism configured to prohibit movement of the blade post relative to the frame member when in a locked position.

10. The retractor assembly of claim 9, comprising a second groove running along the proximal surface of the arcuate connector.

11. The retractor assembly of claim 9, comprising a plurality of mobile carriages engaged to the groove.

12. The retractor assembly of claim 9, comprising a second groove running along the proximal surface of the connector and an additional mobile carriage engaged to the second groove.

13. The retractor assembly of claim 9, wherein the first frame engagement feature is configured to receive a first fastener, wherein the second frame engagement feature is configured to receive a second fastener.

14. The retractor assembly of claim 9, wherein the first frame engagement feature is a thumb screw, wherein the second frame engagement feature is a thumb screw.

15. A retractor assembly for tissue retraction at the site of an incision, the retractor assembly comprising:
an arcuate frame member that extends around an arc and having a first arc terminal end and a second arc terminal end;
a groove running along a proximal surface of the frame member;
a mobile carriage configured to initially engage with the groove, the mobile carriage including:
a blade post holder attached to a blade post; and
a single carriage locking mechanism configure to allow the blade post six degrees of freedom of movement relative to the frame member when in an unlocked position, and to prohibit movement relative to the frame member when in a locked position except translation along the groove.

16. The retractor assembly of claim 15, wherein the arcuate frame member further comprises a first connector engagement feature at the first arc terminal end and a second connector engagement feature at the second arc terminal end.

17. The retractor assembly of claim 16, further comprising:
an arcuate connector having a third arc terminal end, a fourth arc terminal end, a first frame engagement feature at the third arc terminal end configured to reversibly engage with the first connector engagement feature, and a second frame engagement feature at the fourth arc terminal end configured to reversibly engage with the second connector engagement feature.

18. The retractor assembly of claim 17, wherein the arcuate connector further comprises:
a groove running along a proximal surface of the arcuate connector including:
a narrower portion along the proximal surface at the third arc terminal end; and
an expanded portion along the proximal surface at the first arc terminal end.

19. The retractor assembly of claim 18, further comprising:
a second mobile carriage configured to initially engage with the third expanded portion of the second groove and subsequent to an initial engagement, engage with the second narrower portion of the second groove to allow the second mobile carriage to translate along the second groove, the mobile carriage including:
a blade post holder attached to a blade post; and
a carriage locking mechanism configure to allow the blade post six degrees of freedom of movement relative to the arcuate connector when in an unlocked position, and to prohibit movement relative to the arcuate connector when in a locked position except translation along the second groove.

20. The retractor assembly of claim 15, further comprising:
a second mobile carriage configured to initially engage with the groove and subsequent to an initial engagement, engage with the groove to allow the second mobile carriage to translate along the groove; and
a retractor blade assembly comprising a retractor blade and a blade post engaged to the second mobile carriage, and free to yaw, pitch, and roll relative to the second mobile carriage.

* * * * *